United States Patent [19]

Remy et al.

[11] Patent Number: 5,047,416

[45] Date of Patent: Sep. 10, 1991

[54] TRIAZOLE COMPOUNDS AND THEIR USE AS TRANSGLUTAMINASE INHIBITORS

[75] Inventors: David C. Remy, North Wales; John J. Baldwin, Gwyneed Valley; David A. Claremon, Audubon; Stella W. King, Lansdale, all of Pa.

[73] Assignee: Merck & Co., Inc., Rahway, N.J.

[21] Appl. No.: 386,645

[22] Filed: Jul. 31, 1989

[51] Int. Cl.⁵ .................. C07D 249/12; C07D 249/16; A61K 31/41
[52] U.S. Cl. .................................... 514/384; 548/255; 548/264.4; 548/375; 548/251; 546/119
[58] Field of Search ................. 548/255, 263.2, 264.4; 514/384

[56] References Cited

U.S. PATENT DOCUMENTS 4,218,476  8/1980  Jöensson et al. .................. 548/265
4,265,898  5/1981  Horstmann et al. ............... 548/265

OTHER PUBLICATIONS

Kister et al., Can. J. Chem. 57,813 (1979).
Kister et al., Can. J. Chem. 57,822 (1979).

Primary Examiner—Mary C. Lee
Assistant Examiner—Robert C. Whittenbaugh
Attorney, Agent, or Firm—Alice O. Robertson; Hesna J. Pfeiffer

[57] ABSTRACT

Azole compounds including azoles and azolium salts, and their use as transglutaminase inhibitors are disclosed.

14 Claims, No Drawings

TRIAZOLE COMPOUNDS AND THEIR USE AS TRANSGLUTAMINASE INHIBITORS

BACKGROUND OF THE INVENTION

Transglutaminases, also known as transamidases, are a family of enzymes which catalyzes the amide bond formation of the γ-carboxamide group of peptide glutamine residues with an ε amino group of peptide lysine residues.

A number of disease states have been associated with transglutaminase activity. Thus, for example, in acne lesions, transglutaminase activity in sebaceous follicles has been reported by DeYoung et. al., in J. Investigative Dermatology, 82, 275 (1984). Also, the cornified cell envelope in acne has been reported to be a result of transglutaminase activity by Dalziel et. al., Br. J. Exp. Pathology, 65, 107-115 (1984).

Another dermatological disease, psoriasis, is reported to be associated with excessive transglutaminase activity by Bernard et. al. British Journal of Dermatology, 114, 279 (1986).

Cataracts also have been reported to be associated with elevated transglutaminase activities.

Factor XIIIa is a plasma transglutaminase which is the activated form of Factor XIII also known as fibrinase or fibrin-stabilizing factor. It is essential for normal hemostatis and is responsible for the cross-linking of fibrin.

While the activity of this enzyme may be desirable and essential under most circumstances, activity under certain other circumstances can be highly undesirable. Thus, excessive thrombosis, that is the formation of clot within a blood vessel, gives rise to thrombotic strokes, deep vein thrombosis, variant angina, myocardial infarction, and other medical conditions which frequently result in necrosis of tissues and oftentimes in death of a patient. Even if death does not occur, thrombotic attacks are accompanied by damage to cells to which circulation has been prevented by thrombi formation. Removal of the thrombi by lysis is essential and the rate of lysis may be critical in ultimate patient recovery.

Lysis may occur normally in hours or days by the action of a proteolytic enzyme, plasmin, which is present in plasma as the inactive precursor, plasminogen, and which is activated by plasminogen activators, such as (pro)urokinase, urokinase or tissue plasminogen activator (tPA). Since the occurrence of a thrombotic event calls for rapid remedial action, administration of exogenous tissue plasminogen activator or (pro)urokinase is currently looked to in thrombolytic or fibrinolytic therapy. However, a still further reduction in lysis time is necessary to minimize cell injury.

Since Factor XIIIa is an enzyme responsible for the final event in the coagulation of blood, lysis and maintaining the lytic state can be facilitated by the presence of a Factor XIIIa inhibitor. Moreover, the presence of a Factor XIIIa inhibitor as in a prophylactic treatment would inhibit hard clot formation when thrombosis can be anticipated. Thus, a Factor XIIIa inhibitor is useful in inhibiting thrombosis, in treating thrombosis when used with a plasminogen activator or platelet aggregation inhibitor or anticoagulant and in post fibrinolytic therapy in maintaining the lytic state.

STATEMENT OF THE INVENTION

A novel class of azole compounds has been discovered which inhibits transglutaminase activity, particularly, Factor XIIIa activity. For use as Factor XIIIa inhibitors the compounds may be used alone or together with an antithrombotic agents used in thrombolytic or fibrinolytic therapy such as a plasminogen activator, a platelet aggregation inhibitor or an anticoagulant.

DETAILED DESCRIPTION OF THE INVENTION

The azole compound of the present invention is a compound selected from the group consisting of:
(A) an azole represented by the formula

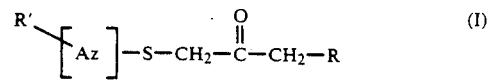

or its acid addition salt, and
(B) an azolium salt represented by the formula

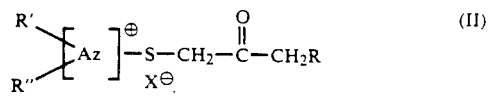

In the foregoing and succeeding formulas,

Az is a 5-membered nitrogen heteroaryl nucleus, optionally condensed, in which at least two nitrogens occupy adjacent positions and all nitrogens are tertiary, R' and R" are independently lower alkyl from 1 to 5 carbon atoms; phenyl; substituted phenyl containing from 1 to 3 substituents selected from lower alkyl, lower alkoxy, halo and hydroxy; benzyl; phenylethyl;

R is hydrogen; lower alkyl from 1 to 5 carbon atoms; cycloalkyl from 3 to 7 carbon atoms; phenyl or substituted phenyl containing from 1 to 3 substituents selected from lower alkyl, lower alkoxy, halo and hydroxy; and X is a negative radical of a pharmaceutically acceptable salt.

"Representative preferred" "Az" nuclei are given below. In addition, the nuclei optionally may have a lower alkyl substituent on a nuclear carbon atom.

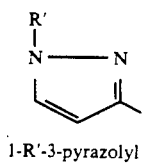 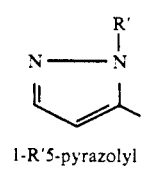

1-R'-3-pyrazolyl          1-R'5-pyrazolyl

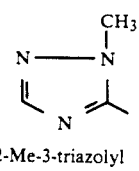 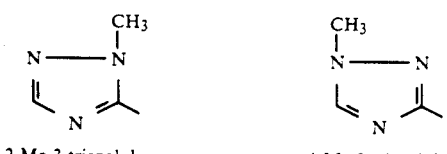

2-Me-3-triazolyl          1-Me-3-triazolyl

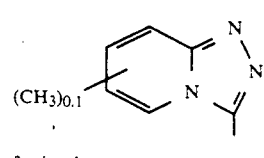 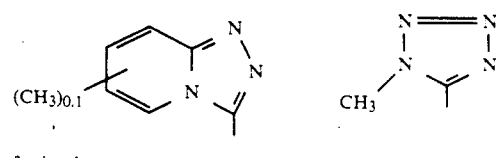

3-triazolo
[4,3,0,1a]-pyridin-3-yl          1-Me-5-tetrazolyl

By the expression "halo" as herein employed is meant fluoro, chloro, bromo and iodo.

Pharmaceutically acceptable salts suitable as acid addition salts as well as providing the anion of the azolium salts are those from acids such as hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methanesulfonic, ethanesulfonic, trifluoromethanesulfonic and the like, and include other acids related to the pharmaceutically acceptable salts listed in Journal of Pharmaceutical Science, 66, 2 (1977) and incorporated herein by reference.

The compounds, both those which are acid addition salts of the compounds represented by formula (I) and those quaternary salts represented by formula (II) are soluble in polar solvents such as methanol, ethanol and the like. The azoles of formula (I) are soluble in nonpolar solvents such as ethyl acetate, methylene chloride, diethylene chloride, carbon tetrachloride, and the like.

The compounds of the present invention are useful as transglutaminase inhibitors, particularly as Factor XIIIa inhibitors, and are adapted to be employed in thrombolytic therapy. In such use, it is administered to a thrombotic patient susceptible to thrombotic attack either alone or in combination.

Preferably, it is employed together with a plasminogen activator, an enzyme which converts plasminogen to plasmin to increase the rate and extent of lysis. Suitable activators include tissue plasminogen activator (tPA), prourokinase (single chain urokinase), urokinase (dual chain urokinase), streptokinase and eminase (European patent application 028,489). The plasminogen activators may be those isolated from natural sources or produced by recombinant technology and include the genetically engineered variants thereof.

Also, it may be employed together with platelet aggregation inhibitors. Platelet aggregation inhibitors may be drugs, naturally occurring proteins or peptides or may be modified or semi-synthetic proteins or peptides. Established drugs which are platelet aggregation inhibitors include aspirin and dipyridamole. Proteins or polypeptides which are platelet aggregation inhibitors have a certain peptide sequence, most frequently Arg-Gly-Asp. Some classes of natural proteins having this property are fibrinogen receptor antagonists, thromboxane receptor antagonists, thromboxane synthesis inhibitors, collagen receptor antagonists and thrombin inhibitors. Among especially useful polypeptides are those designated "Echistatin" and "Bitistatin" and having the amino acid sequence: X-Cys-R-R-R-Arg-Gly-Asp-R-R-R-R-R-Cys-Y where X is H or an amino acid, Y is OH or an amino acid and each R independently is an amino acid, described and claimed in copending applications Ser. No. 184,649, filed Apr. 22, 1988; Ser. No. 303,757, filed Feb. 1, 1989; and Ser. No. 307,642 filed Feb. 7, 1989, all in the names of P. A. Friedman, et. al., the teachings of which are incorporated by reference.

Additionally, the azole compounds may be employed for continued therapy after initial relief from thrombotic attack thereby providing a more complete lysis and minimizing complications from reocclusion. Moreover, the azole compounds may be employed in post thrombosis therapy together with anticoagulants such as heparin and coumarin drugs.

The preferred compounds for use as transglutaminase inhibitors are the quaternary azolium salts.

The compounds to be employed in the practice of the present invention which are azoles may be intermediates in the preparation of those compounds which are azolium salts.

The azoles (I) useful in the present invention may be prepared according to the following equation (1).

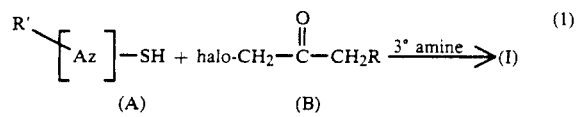

In the preparation of the azole of formula (I), the mercaptoazole (A) starting material, which may be prepared by known procedures hereinafter detailed, is intimately contacted with and caused to react with an acylmethyl halide (B) in the presence of a tertiary amine (3° amine) in an organic solvent at ambient temperature for time sufficient for reaction to take place with the formation of the desired azole of formula (I). After completion of the reaction, the azole may be recovered from the reaction mixture by removing the solvent by evaporation and purifying the residue by conventional procedures.

Tertiary amines suitable in the reaction include triethylamine, trimethylamine, pyridine, picolines, collidines, and the like.

Suitable solvents for the reaction include acetone, methyl ethyl ketone, dimethylformamide, dimethyl sulfoxide and the like.

In carrying out the reaction, a solution of the acylmethyl halide is added to a solution of the mercaptoazole and tertiary amine and the mixture stirred at room temperature for several hours, conveniently overnight. At the end of this period, the solvent is evaporated and the residue partitioned between water and a water-immiscible organic solvent such as ethyl acetate. The organic solution containing the azole is washed and dried, the azole recovered from the dried solution as residue, and thereafter, purified, preferably by chromatography on silica gel using methanol/chloroform as eluant.

The azole then may be employed in the therapeutic method of the present invention as such or as an acid addition salt, or may be treated as an intermediate and employed in the preparation of the azolium salts.

The acid addition salts may be prepared in a conventional manner such as by intimately mixing the azole and desired acid, preferably in a minimal amount of polar solvent such as ethanol or by other conventional procedures.

The azolium salts may be prepared according to the following equation (2).

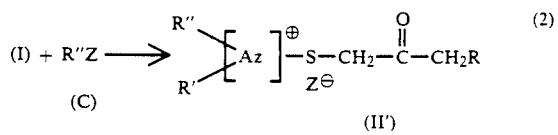

wherein Z is a displaceable group of an active quaternizing agent, and within the definition of X. The reaction is carried out by intimately contacting the reactants in a solvent at ambient temperature for time sufficient for the reaction to take place with the formation of an azolium salt (II'). The azolium salt (II') may be recovered by conventional procedures and purified, if desired, or converted to the ultimate azolium salt by use of an anion exchange resin:

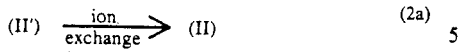 (2a)

The quaternizing agent is preferably alkyl trifluoromethanesulfonate or other active agent. Thus, the halide salts and many other salts are preferably prepared from the trifluoromethanesulfonate.

The reaction may be carried out for from as little as about two hours to a week or so, depending on the particular reactants.

In carrying out the reaction, methyl trifluoromethanesulfonate is added to a solution of the appropriate azole (I) in a non-polar organic solvent such as methylene chloride and the resulting mixture stirred at ambient temperature for time sufficient for substantial completion of the reaction. At the end of this period, the solvent is vaporized and the residue crystallized to obtain the trifluoromethanesulfonate salt or is converted into a halide by ion-exchange chromatography, using methanol/water as solvent. The resulting azolium salt is recovered from the eluate and purified, if desired, by conventional procedures.

The usefulness of the compounds as Factor XIIIa inhibitors for enhancing the rate of clot lysis catalyzed by plasminogen activators may be demonstrated first by establishing the inhibitory potencies of the compounds in a Factor XIIIa assay.

The Factor XIIIa inhibitor assay is based on the incorporation of $^{14}C$-putrescine into casein catalyzed by Factor XIIIa. The assay is carried out employing the procedure described in Methods in Enzymology, Vol. 45, Ch 15., pages 177-191 (1976) and using Factor XIII (F XIII) isolated from human plasma. The procedure is summarized briefly and schematically illustrated as follows:

F XIII
Thrombin
Ca$^{++}$
DTT
↓
-continued
F XIIIa
Control or inhibitor
↓

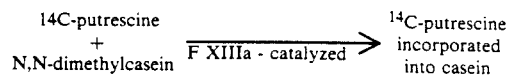

Factor XIII assay mixtures are prepared by adding stepwise, appropriately prepared solutions of thrombin and dithiothreitol (DTT) to a mixture comprising Factor XIII at 140 μg/mL in glycerol/water and tris(hydroxymethyl)aminomethane hydrochloride (Tris•HCl). To a portion of the mixture is added calcium chloride as source of calcium ions required for enzyme activity and to the remaining mixture is added, instead of calcium ions, ethylenediaminetetraacetic acid (EDTA) which serves as a blank for background.

A substrate mixture is prepared from $^{14}C$-putrescine and N,N-dimethylcasein.

The assay tubes and control tubes are charged with the substrate mixture and incubated at 37° C. for 20 minutes. Samples are withdrawn from each tube, spotted onto a filter disk which is then immersed in ice cold trichloroacetic acid solution to precipitate the casein on the filter. The filter is then washed to remove unincorporated or free $^{14}C$-putrescine and after drying is counted for $^{14}C$-putrescine incorporated to casein from which percent activity and/or inhibition can be calculated.

Azole compounds showing at least 50 percent activity at $2 \times 10^{-5}M$ in the Factor XIIIa assay are considered to be useful in inhibiting hard clot formation, in lysing soft clots or especially in supplementing fibrinolysis by plasminogen activator.

The azoles and azolium salts seen in Table I are representative of compounds having IC$_{50}$ at concentrations below $2 \times 10^{-5}M$. Also seen in Table I are the properties of the various compounds.

TABLE I

| Comp No. | [Az]—R' | [Az]⟨R' R'' | R | Anion or Salt | M.P. °C. |
|---|---|---|---|---|---|
| 1 | N—N, N=N, N-CH$_3$ (structure) | — | H | — | — |
| 1a | — | N—N$_\oplus$-CH$_3$, N=N, N-CH$_3$ (structure) | — | Cl$^-$ | 102-104° |
| 2 | CH$_3$—N, N (structure) | — | H | — | — |

TABLE I-continued

| Comp No. | $\left[\text{Az}\right\langle{}^{R'}$ | $\left[\text{Az}\right\langle{}^{R'}_{R''}$ | R | Anion or Salt | M.P. °C. |
|---|---|---|---|---|---|
| 2a | — | (CH₃-N-N=N⊕-CH₃ pyrazolium) | — | Cl⁻ | 179-180° |
| 3 | (1-phenyl-tetrazole) | — | H | — | — |
| 3a | — | (1-methyl-4-phenyl-tetrazolium) | — | Cl⁻ | Foam |
| 4 | (1-methyl-1,2,4-triazole) | — | H | — | — |
| 4a | — | (mixture of two methylated triazolium isomers) | H | CF₃SO₃⁻ | Oil |
| 5 | (6-methyl-[1,2,4]triazolo[4,3-a]pyridine) | — | H | — | — |
| 5a | — | (mixture of two N-methylated triazolopyridinium isomers) | H | Cl⁻ | 190-193° |

For use in facilitating or supplementing fibrinolytic therapy, the azole compound may be administered in a pre- or post-lytic state alone or in combination therapy. Preferably, it is used in a combination therapy with a plasminogen activator, with a platelet aggregation inhibitor, or with natural and synthetic anticoagulants.

The process for facilitating or supplementing fibrinolytic therapy in prothrombic patients comprises administering a therapeutic dose of an azole compound in an amount to provide between 1.4–140 mg/kg/day while considering patient's health, weight, age and other factors which influence drug response. The drug may be administered per os or by injection, and if by injection, either by single injection, multiple injections or continuous infusion.

In the preferred process of the present invention, the azole compound is administered with a plasminogen activator in a combination therapy. When combination therapy is employed, it is preferable to administer the Factor XIIIa inhibitor azole compound first in a single bolus and thereafter to administer the plasminogen activator by continuous infusion. However, both may be administered simultaneously as a continuous infusate. Under certain circumstances it may be desirable to administer the azole compound subsequent to the administration of the plasminogen activator. It is intended that the method of the present invention embrace concurrent administration as well as sequential administration, in any order.

When the Factor XIIIa inhibitor azole compound and plasminogen activator are employed in a combination therapy, it is most desirable to use the plasminogen activator in the dose range of about 500 to 10,000 I.U./kg/minute for from about 30 to 180 minutes and the azole compound in the range of 1 μg-100 μg/kg/minute for a day (1440 minutes).

When the azole compound is to be used with a platelet aggregation inhibitor in combination therapy, the dose range for platelet aggregation inhibitor depends on the nature of the inhibitor. When the platelet aggregation inhibitor is aspirin, the aspirin may be employed at a dose 25-325 mg twice a day. When the platelet aggregation inhibitor compound is dipyridamole, the dipyridamole may be employed at a dose of 25-100 mg four times a day. When the platelet aggregation inhibitor is a semi-synthetic peptide such as "Echistatin" or "Bitistatin", the peptide may be administered in a dose range of 0.1 to 1 nanomole/kg/minute for from 30 to 180 minutes. In each case, the azole compound may be employed in the range of 1-100 μg/kg/minute for a day. The administration may be carried out simultaneously or sequentially in any order as in the procedure for administration with plasminogen activators.

When the azole compound is to be used with heparin, heparin may be administered at doses of 4000 to 8000 units per 4 hours and the azole compound in the range of 1-100 μg/kg/minute for a day. When it is to be used with coumarin drugs, these drugs are administered orally at doses of 10 to 15 mg/kg/day and the imidazole compound administered by infusion at a rate of 1-100 μg/kg/minute for a day.

Compositions to be employed in the practice of the present invention may be a parenteral, oral or suppository compositions comprising an azole compound in a pharmaceutically acceptable carrier.

Parenteral compositions comprise the azole compound in sterile physiologically acceptable media such as physiological saline. Such compositions may also contain other ingredients for purposes such as for aiding solubility or for preservation or the like, said ingredients being those acceptable for intravenous administration. The compositions may be prepared as concentrate compositions and lyophilized and then diluted to the appropriate treating composition immediately prior to administration. A therapeutic composition as a unitary dose form may contain from 100 mg to 10 grams of the azole compound. Compositions suitable in the preferred practice of the present invention of co-administering plasminogen activator and Factor XIIIa inhibitor azole compound may contain from 58 million I.U. of a plasminogen activator and from 100 mg to 10 grams of the azole compound as the Factor XIIIa inhibitor compound.

Oral compositions also may be prepared with the active ingredient in admixture with a pharmaceutically acceptable carrier. Suitable carriers for liquid compositions include water, glycols, oils, alcohols, flavoring agents, preservatives, coloring agents and the like; for solid preparations, starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed.

Suppository compositions may be prepared with ointments, jellies, carbowax, polyethylene sorbitan monastearate, polyethylene glycol, cocoa butter and other conventional carrier material.

The preparation of the azole compounds suitable for inhibiting transglutaminase enzymes, particularly Factor XIIIa, and compositions suitable for carrying out the process of the present invention are illustrated by the following examples but are not to be construed as limiting.

EXAMPLE I

A. 5-Acetonylthio-1-methyl-tetrazole

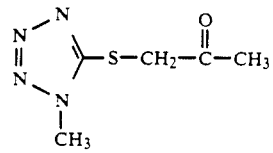

To a solution of 3.12 g (0.02 mol) of 5-mercapto-1-methyltetrazole sodium salt hydrate in 60 ml of absolute ethanol was added dropwise, 2.06 g (0.2 mol) of chloroacetone. After stirring for 20 hours at room temperature, the ethanol was evaporated in vacuo. The residue was dissolved in methylene chloride and was washed with water and then brine prior to drying over Na$_2$SO$_4$. Evaporation of the methylene chloride solution gave 1-methyl-5-acetonylthiotetrazole that was purified by flash chromatography on silica gel to yield 0.94 g of the 5-acetonylthio-1-methyltetrazole product.

B. 5-Acetonylthio-1,4-dimethyltetrazolium chloride

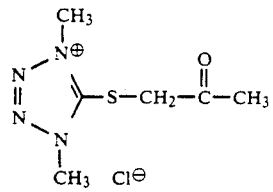

The 5-acetonylthio-1-methyltetrazole, prepared as above described, was dissolved in 20 ml of methylene chloride and to the resulting solution was added 0.617 gram (0.0055 mol) of methyl trifluoromethanesulfonate and the mixture allowed to stand overnight at room temperature. Thereafter, the solvent was vaporized off and an oily residue obtained. The latter was dissolved in aqueous methanol and the methanol solution passed over a Dowex-1 (Cl$^-$) ion exchange column. The eluate from the column was evaporated to obtain a waxy material which was triturated with hexane to obtain a waxy solid which after drying in high vacuum amounted to 0.80 gram of 5-acetonylthio-1,4-dimethyltetrazolium chloride, m.p. 102°-104° C.

Anal. Calcd for C$_6$H$_{11}$ClN$_4$OS: C, 32.36; H, 4.98; N, 25.16

Found: C, 32.11; H, 5.40; N, 25.45

EXAMPLE II

A. 3-Acetonylthio-4-methyltriazole

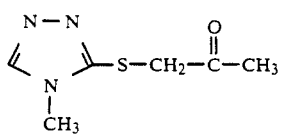

To a solution of 2.3 g (0.02 mol) of 4-methyl-4H-1,2,4-triazole-3-thiol and 2.5 g (0.025 mol) of triethylamine in 100 ml of acetone was added dropwise 2.06 g (0.02 mol) of chloroacetone and the mixture was stirred for 20 hours at room temperature. The mixture was evaporated in vacuo to obtain a residue which was dissolved in methylene chloride. The methylene chloride solution was washed with water and dried over sodium sulfate; the solvent was vaporized from the dried solution to obtain the desired 3-acetonylthio-4-methyltriazole.

B. 3-Acetonylthio-1,4-dimethyltriazolium methanesulfonate and 3-Acetonylthio-2,4-dimethyltriazolium methanesulfonate

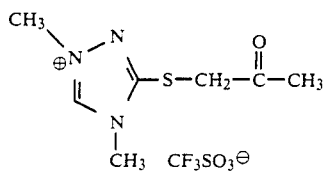

and

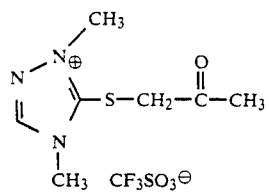

A solution of 0.171 gram (0.001 mol) of the 3-acetonylthio-4-methyltriazole prepared in Part A and 0.113 gram (0.001 mol) of methyl trifluoromethanesulfonate in 2 milliliters of methylene chloride was stirred at room temperature for two hours. The solvent was evaporated from the mixture to obtain a hygroscopic oil. The latter was dried in high vacuum to obtain a product which was determined by NMR spectroscopy to be a mixture of 82% 1,4-dimethyl-3-acetonyltriazolium methansulfonate and 18% 2,4-dimethyl-3-acetonylthiotriazolium methanesulfonate.

Anal. Calcd for $C_8H_{12}F_3N_3O_4S_2 \cdot \frac{1}{2}H_2O$: C, 27.90; H, 3.81; N, 12.20

Found: C, 27.63; H, 3.85; N, 11.95

EXAMPLE III

A. 3-Acetonylthio-6-methyltriazolo[4,3-a]pyridine

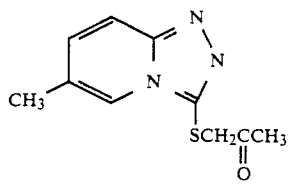

A solution of 0.215 g (0.0013 mol) of 6-methyltriazolo[4,3-a]pyridine-3-thiol and 0.164 g (0.00163 mol) of triethylamine in 15 ml of acetone was intimately mixed with 0.134 g (0.0013 mol) of chloroacetone as described in Example II. The material obtained was purified by flash chromatography on silica gel using 1% $CH_3OH$ in $CHCl_3$ to obtain 0.24 gram of product.

B. 3-Acetonylthio-1,6-dimethyltriazolo[4,3-a]pyridinium chloride and 3-Acetonylthio-2,6-dimethyltriazolo[4,3-a]pyridinium chloride

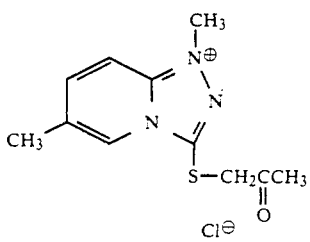

and

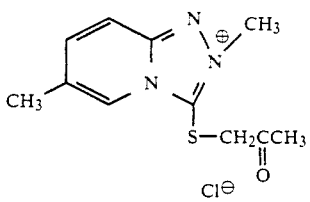

A solution of the 0.24 g of product (above obtained) in 7 ml of methylene chloride was mixed with 0.123 ml (0.00148 mol) of methyl trifluoromethanesulfonate and allowed to stand for 2 hours. Then, the solvent was evaporated and the oily residue was dissolved in 20% methanol in water and passed over a Dowex 1 (Cl⁻) ion exchange column. The eluate was evaporated and the residue triturated with isopropyl alcohol to induce crystallization. The solid was removed by filtration and dried. This product was found by NMR spectroscopy to be a mixture of 93.5% of (1,6) and 6.5% of (2,6)-dimethyl-3-acetonylthiotriazolo[4,3-a]pyrdinium chloride, m.p. 190°–193° C.

Anal. Calcd for $C_{11}H_{14}ClN_3OS$ C, 48.61; H, 5.19; N, 15.46

Found: C, 48.69; H, 5.34; N, 15.06

EXAMPLE IV

In operations carried out in a manner similar to that described in the foregoing examples, the following compounds are prepared:

TABLE II
| [Az−R']  | [Az⟨R'/R''] | R | Anion or Salt |
|---|---|---|---|
|  |  | −CH(CH₃)₂ | HCl |
|  |  | " | CF₃SO₃⁻ |
| 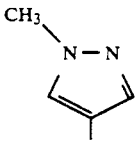 |  | −C₆H₅ | — |
|  | 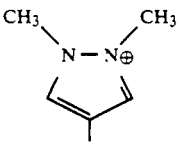 | −C₆H₅ | CF₃SO₃⁻ |
| 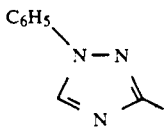 |  | −C₄H₉n | HCl |
| 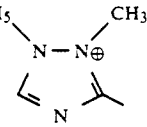 |  | 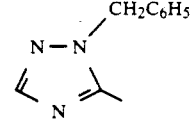 | HCl |
|  | 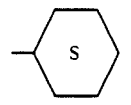 | −CH₃ | CF₃SO₃⁻ |
|  |  | 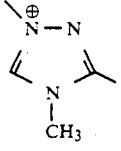 | — |
|  | 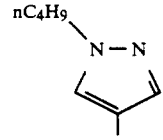 | " | CF₃SO₃⁻ |
| 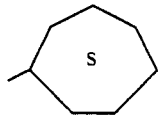 | — | −CH₂CH₂C₆H₅ | HCl |

TABLE II-continued

| $\left[\text{Az}\right]\diagdown^{R'}$ | $\left[\text{Az}\right]\diagdown^{R'}_{R''}$ | R | Anion or Salt |
|---|---|---|---|
| | CH₂C₆H₅ ![pyridine-hydrazone with N-CH₃⊕] | —CH₂CH₂C₆H₅ | CF₃SO₃⁻ |
| (CH₃)₂CH-N-N=/=N (triazole, isopropyl) | | ⟨S-cyclohexyl⟩ | — |
| | (CH₃)₂CH, CH₃ on N-N⊕ triazolium | ⟨S-cyclohexyl⟩ | Cl⁻ |

EXAMPLE V

Parenteral Composition

One liter of a parenteral composition comprising one of the foregoing compounds may be prepared from the following formulation:

| | Grams |
|---|---|
| Azolium salt | 5.0 |
| Polysorbate 80 | 2.0 |
| Sodium Chloride | 9.0 |
| Sodium carboxymethyl cellulose | 10.0 |
| Methyl paraben | 1.8 |
| Propyl paraben | 0.2 |
| Water, USP q.s. to 1 liter | |

The parabens, sodium chloride and carboxymethylcellulose are dissolved in one-half the total volume of water by heating to 95° C. to obtain a solution which is then filtered and autoclaved. The polysorbate is dissolved in one-third of the total volume of water, and the resulting solution also filtered and autoclaved. Sterile active ingredient is added to the second solution and the mixture passed through a sterile colloid mill to obtain a suspension of active ingredient. The first solution is added to the suspension with stirring then U.S.P. water added to 1 liter. Sterile vials are filled with the suspension while stirring.

EXAMPLE VI

Oral Composition 5000 compressed tablets, each containing as active ingredient 100 milligrams of one of the foregoing compounds, may be prepared from the following formulation:

| | Grams |
|---|---|
| Azolium salt | 500 |
| Starch | 700 |
| Dibasic calcium phosphate hydrous | 5000 |
| Calcium stearate | 25 |

The ingredients are finely powdered, mixed well, and then granulated with 10 percent starch paste. The granulation is dried and compressed into tablets using starch as a disintegrant and calcium stearate as lubricant.

Preparation of the Starting Materials

When the starting material is a 1-alkyl-3-mercaptopyrazole, it may be obtained by reacting 2-chloroacrylonitrile with R'NHNH₂ in the presence of aqueous potassium carbonate to obtain a 1-alkyl-3-aminopyrazole which then may be diazotized, coupled with canthate and thereafter hydrolyzed in aqueous sodium or potassium hydroxide.

The preparation of the 1-alkyl-3-aminopyrazole may be carried out as described in Synthesis, page 52 (January, 1976) and the preparation of the 1-alkyl-3-mercaptopyrazole from the aminopyrazole may be carried out as described in U.S. Pat. No. 4,275,073, the teachings of which are incorporated by reference.

When the starting material is a mercaptopyrazole, it may be prepared by the reaction of potassium hydrogen sulfide or potassium or sodium sulfide on an appropriate 3 or 5 halo pyrazole or by the reaction of potassium hydrogen sulfide on the appropriate pyrazoline-5-one. Alternatively, the pyrazoline-5-one may be caused to react with phosphorus oxychloride to produce a 5-chloropyrazole which then may be caused to react with potassium hydrogen sulfide to produce the mercaptopyrazole starting material. The conditions for preparation of related compounds are summarized in "Heterocyclic Compounds, Pyrazolines, Pyrazolidones and Derivitives", pgs 58–9, John Wiley and Sons (1964) and references cited therein. The 2-pyrazoline-5-ones may be prepared by the heating together and condensing a β-keto ester with an appropriate hydrazine. The pyrazolone then may be reacted with phosphorus oxychloride to obtain a halopyrazole or be reacted directly with phosphorus pentasulfide or equivalent as summarized in the aforecited reference at page 14 and page 27 and in the references cited therein which are incorporated by reference.

When the starting material is a mercaptotriazole, it may be prepared from an appropriately substituted thiosemicarbazides which is cyclized to a triazole by heating with formic acid or formate according to the following equation

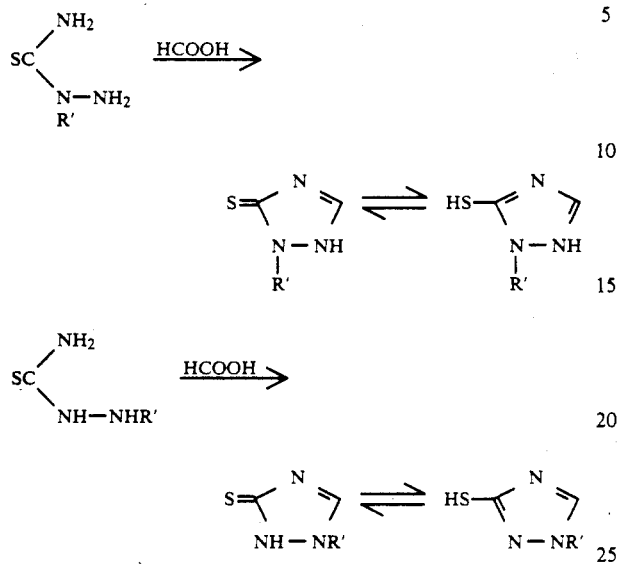

as more fully described in "Heterocyclic Compounds, Triazoles" Vol 37, page 405, John Wiley & Sons, Inc. 1981, and references cited therein and which is incorporated by reference.

When the starting material is a mercaptotetrazole, it may be prepared by the reaction of potassium hydrogen sulfide on the appropriate halotetrazole employing procedures similar to that for the pyrazoles. The 1-methyl-5-tetrazolylthiol is commercially available.

When the starting material is a 3-triazolo[4,3-a]pyridin-3-ylthiol, it may be prepared by warming together an appropriate 2-pyridylhydrazine with carbon disulfide in chloroform solution until the evolution of hydrogen sulfide ceases with the formation of the thiol product as a solid. The latter may be recovered and then purified by crystallization as more fully described by K. T. Potts et al. J. Org. Chem. 1966, 251, 259.

What is claimed is:

1. An azole compound selected from the group consisting of:

(A) an azole represented by the formula

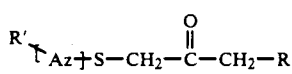

or its acid addition salt,
wherein said acid addition salt is a salt formed by the addition of an acid selected from the group consisting of hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methanesulfonic, ethanesulfonic, and trifluoromethanesulfonic acids; and (B) an azolium salt represented by the formula

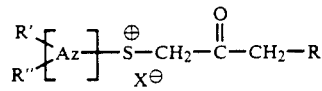

wherein Az is a triazole nucleus,

R' and R" independently are lower alkyl from 1 to 5 carbon atoms, phenyl; substituted phenyl containing from 1 to 3 substituents selected from lower alkyl, lower alkoxy, halo and hydroxy; benzyl, phenylethyl, R is hydrogen, lower alkyl from 1 to 5 carbon atoms, cycloalkyl from 3 to 7 carbon atoms, phenyl or substituted phenyl containing from 1 to 3 substituents selected from lower alkyl, lower alkoxy, halo and hydroxy; and X is a negative radical of a pharmaceutically acceptable salt;

wherein said negative radical is derived from an acid selected from the group consisting of hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methanesulfonic, ethanesulfonic, and trifluoromethanesulfonic acids.

2. A compound according to claim 1 which is an azolium salt.

3. 3-Acetonylthio-1,4-dimethyltriazolium methanesulfonate or 3-acetonylthio-2,4-dimethyltriazolium methanesulfonate or a mixture thereof.

4. A composition suitable for thrombolytic therapy in inhibiting or combatting thrombosis or for supplementing fibrinolytic therapy comprising an amount of an azole compound of claim 1 in a pharmaceutically acceptable carrier.

5. A composition according to claim 4 in unit dose form wherein the azole compound is present in amount of 100 mg to 10 grams.

6. A composition suitable for thrombolytic therapy in unit dosage form comprising (a) a plasminogen activator selected from tPA in an amount of about 58 million I.U. and streptokinase in an amount of 1.5 million I.U. and (b) an azole compound according to claim 1 in an amount of from 100 mg to 10 grams in a pharmaceutically acceptable carrier.

7. A composition according to claim 6 wherein the plasminogen activator is tPA.

8. A composition according to claim 6 wherein the plasminogen activator is streptokinase.

9. A method for inhibiting hard clot formation or supplementing fibrinolytic therapy comprising administering to a patient in need of such treatment an azole compound of claim 1 in an amount effective for inhibiting hard clot formation or supplementing fibrinolytic therapy.

10. A method according to claim 9 wherein the azole compound is administered to provide about 1–100 μg/kg/minute for one day.

11. A method according to claim 9 wherein an antithrombotic agent is also administered.

12. A method according to claim 11 wherein the antithrombotic agent is plasminogen activator.

13. A method according to claim 11 wherein the antithrombotic agent is platelet aggregation inhibitor.

14. A method according to claim 11 wherein the antithrombotic agent is an anticoagulant.

* * * * *